United States Patent [19]
de Broqueville

[11] Patent Number: 5,569,801
[45] Date of Patent: * Oct. 29, 1996

[54] POLYMER CONVERSION PROCESS

[75] Inventor: Axel de Broqueville, Kraainem, Belgium

[73] Assignee: Fina Research, S.A., Feluy, Belgium

[ * ] Notice: The term of this patent shall not extend beyond the expiration date of Pat. No. 5,288,934.

[21] Appl. No.: 156,481

[22] Filed: Nov. 23, 1993

Related U.S. Application Data

[63] Continuation-in-part of Ser. No. 937,637, Aug. 27, 1992, Pat. No. 5,288,934.

[30] Foreign Application Priority Data

Nov. 24, 1992 [BE] Belgium ............................... 09201018

[51] Int. Cl.$^6$ ..................................................... C07C 1/00
[52] U.S. Cl. ........................... 585/241; 585/240; 585/310; 585/324; 585/613; 585/648; 585/653
[58] Field of Search ..................................... 585/240, 241, 585/310, 324, 613, 648, 653

[56] References Cited

U.S. PATENT DOCUMENTS

| | | | |
|---|---|---|---|
| 3,985,820 | 10/1976 | Albright et al. | 585/648 |
| 4,175,211 | 11/1979 | Chen et al. | 585/241 |
| 4,642,401 | 2/1987 | Coenen et al. | 585/241 |
| 4,851,601 | 7/1989 | Fukuda et al. | 585/241 |
| 5,136,117 | 8/1992 | Paisley et al. | 585/241 |
| 5,288,934 | 2/1994 | de Broqueville | 585/241 |

*Primary Examiner*—Glenn Caldarola
*Assistant Examiner*—E. D. Irzinski
*Attorney, Agent, or Firm*—Pamela S. Smith; M. Norwood Cheairs

[57] ABSTRACT

The present invention relates to a process for the conversion of polymers and particularly for the conversion of plastic containers or other plastic wastes. The process requires a minimum number of steps for treating typical industrial plastic wastes. The process comprises placing the mixed polymers in contact with a solvent that dissolves part of the polymers and separates the other fractions. The solvent fraction is subjected to treatment for the recovery of lower molecular weight stream that can be utilized in refining operations or other chemical operations.

13 Claims, 3 Drawing Sheets

POLYMER CONVERSION PROCESS

CROSS-REFERENCES TO RELATED APPLICATIONS

This applications is a continuation-in-part of application entitled "Process for the Conversion of Polymers" filed on Aug. 27, 1992 and assigned Ser. No. 07/937,637, now U.S. Pat. No. 5,288,934.

BACKGROUND OF THE INVENTION

1. Field of the Invention

The present invention relates to the conversion of polymers, particularly of polymer wastes into industrially useful products. More particularly, it relates to the conversion of mixtures of polymers into products of lower molecular weight and especially into light hydrocarbons which can be recycled or employed as raw material.

2. Background

Polymers are produced in continually growing quantities and most are employed in the single-use packaging sector.

However, the polymers' low propensity to natural decomposition, coupled with the decrease in the number of available tipping grounds or land fills, prompts the investigation of other routes for processing the used packages made of polymeric materials.

Incineration, a technique frequently employed for processing household waste, gives good results with polyolefins, whose complete combustion within the rules of the art gives water and carbon dioxide. Incineration is less suitable for other polymers which do not burn as well and tend to carbonize and produce noxious fumes.

Recycling of such polymers has had limited success because after collection, preliminary sorting according to type of polymer is required.

There is therefore a need for a large-scale polymer conversion process, particularly for mixed polymer wastes, into products of lower molecular weight and especially into lighter hydrocarbons which can be recycled or employed as raw material, for example for feeding oil refineries and petrochemical steam crackers.

The behavior of polymers at high temperature, if appropriate in the presence of suitable catalysts or reactants, has been investigated for many years and is well known to those skilled in the art. Depending on the circumstances, it results in a depolymerization (for example during the pyrolysis of polystyrene or the methanolysis or hydrolysis of polyethylene terephthalate) or in a decomposition (for example during the catalytic treatment of polyethylene).

Thus, U.S. Pat. No. 4,151,216 describes the catalytic cracking of polypropylene at 425°–475° C. on silica-alumina, giving a fuel stream which is liquid at 50° C.

U.S. Pat. No. 4,143,086 discloses the catalytic cracking of amorphous polypropylene in a fluidized bed in the presence of a hydrocarbon feedstock, giving an effluent containing propylene.

European patent application No. 414 439 describes the conversion of high molecular weight polymers into products of lower molecular weight by heating the polymer (optionally dissolved) in contact with an acidic zeolite catalyst.

European patent application No. 276 081 and U.S. Pat. No. 4,584,421 describe two-stage polyolefin decomposition processes consisting of a thermal cracking followed by a catalytic cracking of the product of the first reaction.

U.S. Pat. No. 4,108,730 discloses a process for converting relatively ash-free solid polymeric wastes to more valuable liquid, solid, and gaseous products by mixing the polymeric waste at high temperatures in a refractory petroleum stream and catalytically cracking the mixture.

However, these processes do not envisage the treatment of mixtures of various polymers which may contain a high percentage of impurities, and the problems which arise therefrom. It therefore seems important and necessary in these times to have a simple process, comprising a minimum number of steps to treat polymer mixtures.

The Applicant has now developed an integrated process for the conversion of polymers, which process is particularly suitable for the conversion of polymer wastes into industrially useful products.

SUMMARY OF THE INVENTION

According to the present invention, the polymer conversion process comprises the steps of:

(1) placing the polymers, ground or not, in contact with a solvent made up of a hydrocarbon cut which has a boiling temperature higher than 180° C. and is composed predominantly of aromatic hydrocarbons;

(2) extraction of any formed decomposition gases;

(3) recovery of a polymer solution from which most of the dense and light insoluble wastes have been removed; and (4) treatment of this polymer solution by a cracking process chosen from thermal cracking and catalytic cracking.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Figure 1:
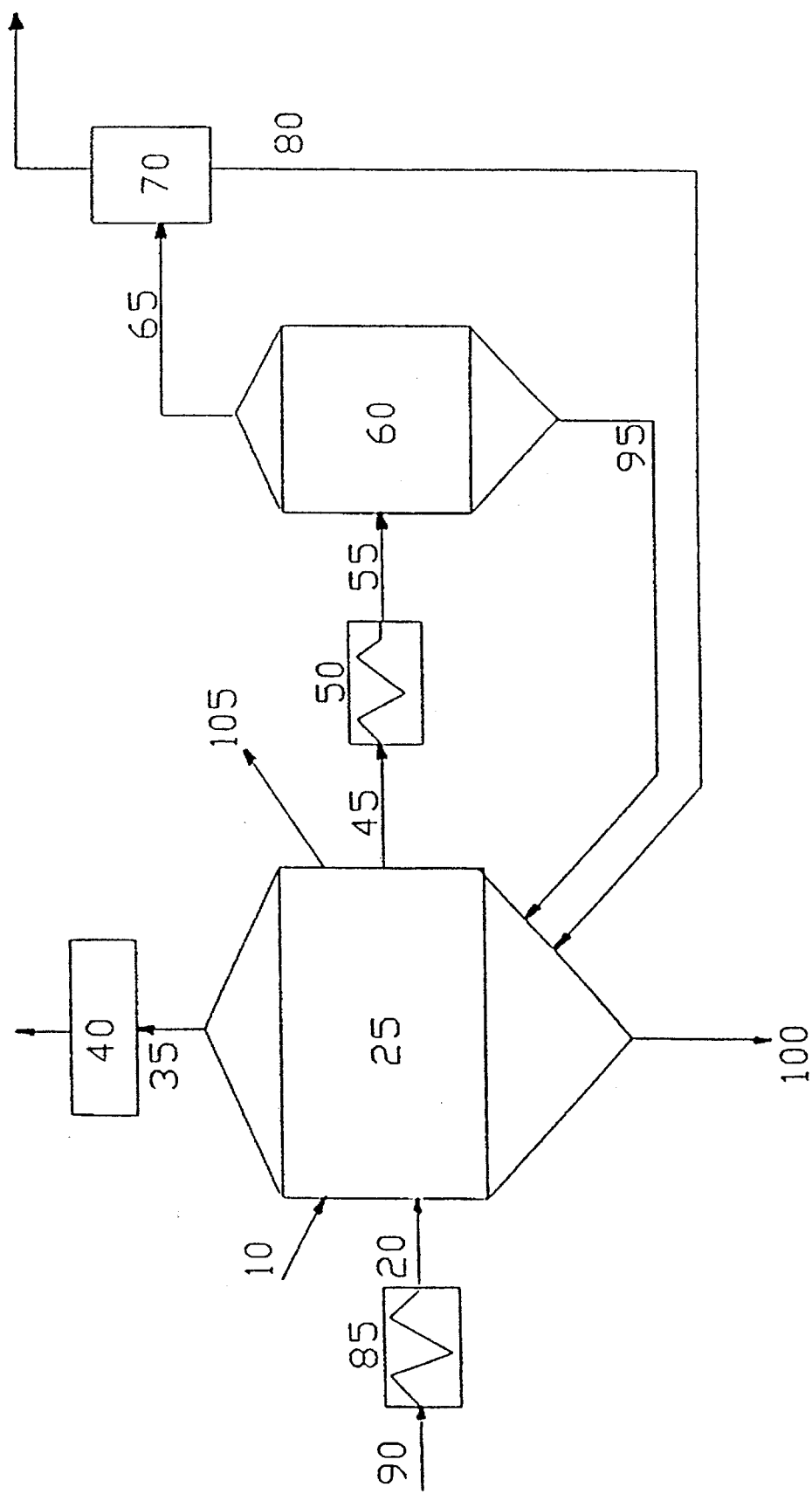
FIG. 1 represent an embodiment of the invention wherein the mixture of ground polymer wastes is conveyed into contact with a solvent for heating, mixing and separation. The formed gases are separated as are any insoluble fractions. The soluble fraction is subjected to thermal cracking from which a lower molecular weight hydrocarbon stream is recovered.
Figure 2:
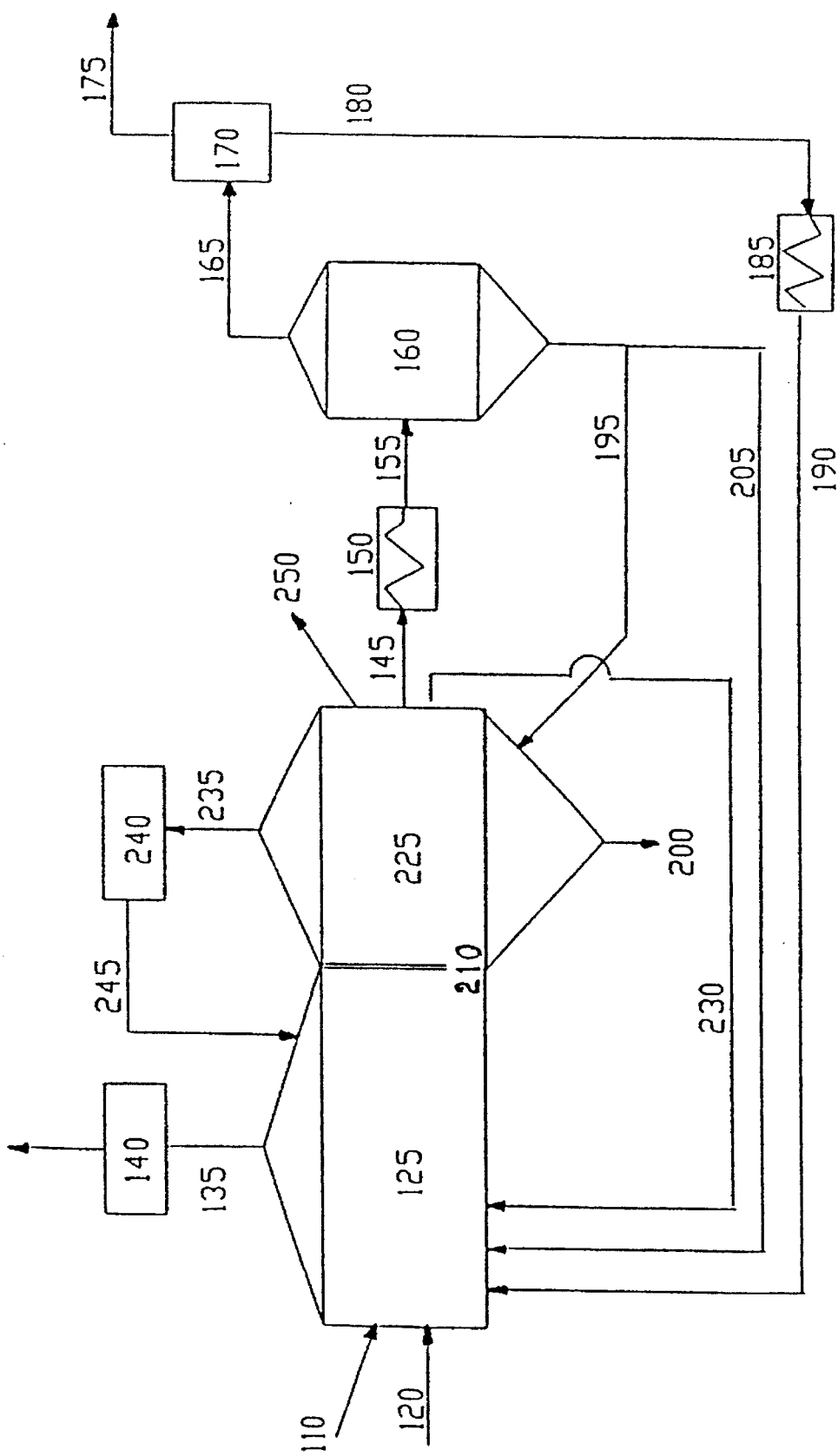
FIG. 2 represents another embodiment of the invention wherein the mixing and heating of the polymeric waste stream with the hydrocarbon solvent is achieved in two stages to allow the handling of different types of polymers.
Figure 3:
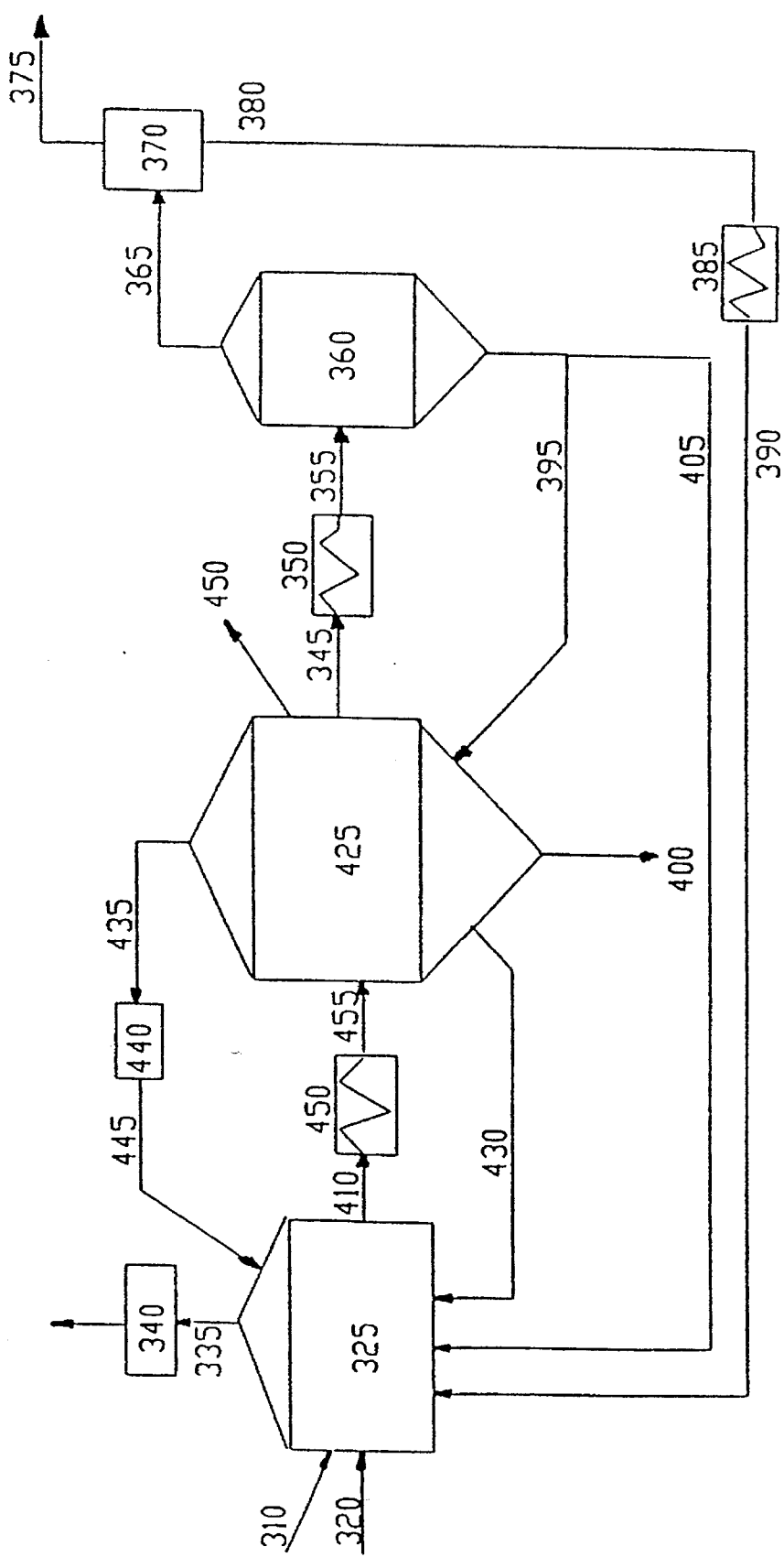
FIG. 3 represents another embodiment of the invention wherein an external heater is added between the mixer and separator.

The process of the present invention is particularly useful for the treatment of soiled packaging wastes. These polymeric waste streams usually comprise the following polymers:

high and low density polyethylene (PE)

polypropylene (PP)

polystyrene (PS)

polyvinyl chloride (PVC)

polyethylene terephthalate (PET)

For the purposes of the present invention, these polymers, recovered in the form of films, hollow bodies (containers), food trays, or foam, are not generally sorted. It may be desirable to subject the polymeric feed to a size reduction step prior to the addition of the solvent stream. A variety of size reduction means are well known in the art and any of these means may be employed in the process of the present invention. For example, the polymeric material can be shredded or ground into powder or chips to reduce the dissolving time. Although this process does not require any washing, the polymeric material may be cleaned to remove the nonpolymeric fractions (paper, metal, etc.). In fact, after a sufficiently long residence in a vessel at more than 120° C., the organic wastes and other insoluble debris (paper, metal, glass, and the like) can be easily separated from the solution by various means including settling, filtering or centrifuging. The separated material can be incinerated and dumped.

According to one embodiment of the invention, the polymer mixture is placed in contact with a solvent consisting of a hydrocarbon cut which has a boiling temperature higher than 180° C. and is composed predominantly of aromatic hydrocarbons. Its relative density or specific gravity is lower than 1 and preferably from 0.88 to 0.98 or, even more preferably from 0.92 to 0.96. The preferred solvent is cycle oil, light (distilling between 180° and 350° C.) or heavy (distilling from 350° C. onwards) or else any mixture thereof. Preferably, the solvent is light cycle oil (LCO) distilling between 250° and 350° C. The solvent preferably has a ratio of monocyclic to bicyclic aromatic hydrocarbons of between 2:1 and 1:2, preferably approximately 1:1.

According to another embodiment of the present invention, dissolving the polymeric material is carried out in one stage. The preferred operating conditions include a temperature ranging from 120° to 350° C., depending on the solvent employed. Thus, the work will preferably be done at a temperature of 150° to 200° C. with light cycle oil as solvent. The flow rates of ground polymers and of solvent and the contact time are adjusted so that the soluble polymers are practically completely dissolved to give a solution which is as concentrated as possible (generally containing from 10 to 20% by weight of polymer).

After mixing and settling, the following fractions are recovered:

(a) an insoluble light fraction at the surface, (b) an insoluble heavy fraction at the bottom, (c) solid particles in suspension, and (d) a solution of polymers.

According to another embodiment of the present invention, dissolving the polymeric material is carried out in two stages, the first at a temperature of approximately 120° to 250° C., preferably from 150° to 200° C., the second at a temperature of approximately 250° to 400° C., preferably approximately 300° C.

In the first stage a heated solvent such as light cycle oil (LCO), heavy cycle oil (HCO) or a mixture of the two is introduced, as also is the plastic waste. The mixture can also be heated using an external heat source. As soon as the temperature exceeds approximately 120° C. any polyvinyl chloride (PVC) which may be present melts and decomposes, by an autocatalytic reaction, giving hydrochloric acid and a hydrocarbon backbone containing unsaturated bonds. According to a preferred embodiment of the invention the acid released is neutralized, for example with calcium oxide. The solution containing PVC may also be treated to saturate all or a portion of the unsaturated bonds in the hydrocarbon backbone, for example by dienophile addition. The other polymers present in the mixture melt or decompose or are recovered with the other insolubles in suspension in the solution which is generally very viscous and stirred.

This mixture is conveyed to the second stage where, after lowering the viscosity by raising the temperature to a value of between 250° C. and 400° C., depending on the solvent employed, and after the usual mixing, settling and similar operations, the light fraction which is insoluble in the solvent is recovered at the surface of the latter, whereas the solvent-insoluble heavy fraction is recovered at the bottom. The heavy fraction (having a higher specific gravity than the solvent solution) removed includes especially the calcined organic matter, glass, sand, stones, metal particles, nonfusible high-density polymers and suspended particles which have settled.

Whatever the particular embodiment chosen for the dissolving stages, at least one polymeric material dissolved as described above is converted into products of lower molecular weight.

According to one embodiment the polymer solution is heated and is conveyed into a thermal cracking reactor. The main product of this reaction is a mixture composed essentially of normally liquid hydrocarbons, which can be recycled to an oil refinery or into petrochemical steam crackers. The light cycle oil is not very sensitive to thermal cracking and, after separation, can be recycled into the process of the invention, as can the heavy cracked hydrocarbon whose distillation temperature is comparable to that of the solvent. Alternatively, these hydrocarbons are recycled for cracking into lighter fractions.

According to another embodiment the cracking is carried out in a catalytic cracking reactor. The catalysts employed, the reaction conditions and the products obtained are well known (for example as disclosed in European Patent Application No. 414 439) and will not be described in detail here. The products, chiefly normally liquid hydrocarbons, may be recovered, purified and employed as raw material in oil refining or in petrochemical steam crackers. The light cycle oil is not very sensitive to catalytic cracking and, after separation, may be recycled into the process of the invention. It is to be understood that various modifications can be introduced into the embodiments of the process described above without departing thereby from the scope of the invention. Thus, the process of the invention can function continuously or noncontinuously or semicontinuously (for example when dissolving the polymeric material is carried out noncontinuously and the remainder of the operations continuously).

An advantage of the process of the invention lies in the use of a solvent which is at present of little recoverable value in refineries.

The invention will now be described in greater detail with reference to FIGS. I to III, each of which diagrammatically represents one particular embodiment among the many that are possible.

In FIG. I the mixture of packaging polymer wastes which have been ground is conveyed by the feed system 10 into a mixer 25 where it is brought into contact with a cycle oil (LCO, HCO or any mixture thereof) which is delivered via the pipeline 90, heated in 85 and introduced via the pipeline 20. After mixing and separation, the insoluble light fraction is recovered at the surface and removed at 105, whereas the insoluble dense fraction is removed via the conduit 100.

The hydrochloric acid vapor which may be formed is conveyed via the conduit 35 into a neutralization system 40.

The fraction including the solvent and the polymers which are dissolved in it, after optional filtration, is recovered at 45, heated in 50 and conveyed via the conduit 55 into a thermal cracking reactor 60, from which a mixture of hydrocarbons of lower molecular weight is recovered at 65 and the uncracked components are recovered at 95 and recycled via the conduit 95. The hydrocarbons of lower molecular weight can be separated in 70 into a heavy fraction containing the solvent which is recycled via the conduit 80 and into a light fraction 75.

In a second embodiment, described in FIG. II, the mixer (25) is divided into two parts, 125 and 225, connected together by an opening 210.

The mixture of polymer waste is conveyed via the feed system 110 into a mixer 125 where it is brought into contact with a light and/or heavy cycle oil (LCO, HCO or any mixture thereof) delivered via the pipeline 120.

After mixing and holding at a temperature of approximately 150° to 200° C., most of the polymers are dissolved and the PVC is decomposed, giving off hydrochloric acid vapor which is conveyed via the conduit 135 into a neutralization system 140. The mixture is transferred via the opening 210 into a separator 225, where it is heated to a temperature of 250° to 300° C. After separation, the insoluble heavy fraction is removed via conduit 200 and the insoluble light fraction is recovered at the surface and removed at 250.

The fraction including the solvent and the polymers which are dissolved in it, after optional filtration, is recovered at 145, heated in 150 and conveyed via conduit 155 into a thermal cracking reactor 160, from which a mixture of hydrocarbons of lower molecular weight is recovered at 165 and the uncracked components are recovered at 195 and 205 to be recycled via conduits 195 and 205 towards the separator 225 and the mixer 125 respectively. This recycling makes it possible to heat the separator and the mixer and to maintain them at the desired temperature. Recycling from the separator 225 towards the mixer 125 is also possible via the pipeline 230.

The hydrocarbons of lower molecular weight are separated in 170 into a light fraction 175 and a heavy fraction 180 which is reheated in 185 and recycled into the mixer 125 via the pipeline 190.

The hydrocarbons which evaporate in the separator 225 are removed via the pipeline 235, are cooled and condensed in 240 and are recycled into separator 125 via conduit 245. The light insolubles floating at the surface of the separator are removed at 250.

This method of dissolving in two stages makes it possible to crack the PVC at a lower temperature in a first vessel and to complete the dissolving of the other polymers and the calcination of the organic materials at higher temperature in a second vessel in the absence of oxygen. The higher temperature makes it possible to reduce the viscosity in order to improve the separation of the insoluble dense fractions.

In a third diagram, FIG. III, the mixer 325 and the separator 425 are separated by a heater 450. Heating means using an external heat source may be provided for the mixer, the separator and the reactor. Alternatively, the temperature can be maintained by the recycled fractions.

EXAMPLE 1

A mixture of soiled and ground, used packaging wastes was taken, comprising, by weight:

| | |
|---|---|
| low density polyethylene | 30% |
| high density polyethylene | 20% |
| polypropylene | 20% |
| polystyrene | 14% |
| PVC | 8% |
| PET | 8% | and being in the form (by weight) of:

| | |
|---|---|
| bottles, hollow bodies | 38% |
| food trays | 21% |
| film | 30% |
| foam | 11% |

The waste was treated according to the embodiment described by FIG. I. The solvent was light cycle oil (220°–350° C., 70% aromatics, with monocyclics:bicyclics ratio equal to 1:1, a relative density of 0.94). The temperature in reactor 115 was 200° C. Reactor 120 had a temperature of 300° C. The residence time was half an hour in each reaction. Calcium oxide was employed to neutralize the hydrochloric acid. The cracking reactor was a thermal cracking reactor operated at 400° C. A mixture of hydrocarbons which had the following distillation curve was obtained:

| | |
|---|---|
| 100–221° C. | 15% by weight |
| 221–350° C. | 70% by weight |
| residue at 350° C. | 15% by weight |

I claim:

1. A process for the conversion of polymers into lighter hydrocarbon streams comprising the steps of:
   (1) contacting the polymers with a solvent comprising a hydrocarbon cut having a boiling temperature higher than 180° C. and composed predominantly of aromatic hydrocarbons, the polymers comprised of one or more members selected from the group consisting of polyethylene, polypropylene, polystyrene, polyvinyl chloride and polyethylene terephthalate;
   (2) dissolving a portion of the polymers in the solvent;
   (3) recovering (i) a top layer of undissolved particles, (ii) a bottom layer of undissolved heavy particles, and (iii) a solvent layer containing dissolved polymers and suspended particles of polymers; and
   (4) cracking the solvent layer to recover lower molecular weight products.

2. The process of claim 1 further comprising the step of removing any decomposition gases formed in the contacting and dissolving steps prior to the recovering step.

3. The process according to claim 1, wherein said solvent is a light cycle oil which has a boiling temperature of between 220° and 350° C.

4. The process according to claim 1, wherein said solvent is a hydrocarbon cut which has a boiling temperature higher than 350°.

5. The process according to claim 1, wherein said solvent is a mixture of light cycle oil and of heavy cycle oil.

6. The process according to claim 1, wherein the solvent has a ratio of monocyclic to bicyclic aromatic hydrocarbons from 2:1 to 1:2.

7. The process of claim 1, wherein step (4) is comprises thermal cracking.

8. The process of claim 1 wherein the polymers include polyvinyl chlorides.

9. The process according to claim 1, further including the step of neutralizing acid created in the contacting and dissolving steps.

10. The process according to claim 1 further including the step of saturating all or a portion of unsaturated bonds in the solvent layer.

11. The process according to claim 1 wherein the dissolving step further comprises a first heating stage at a temperature of approximately 120° to 250° C., and a second heating stage at a temperature of approximately 250° to 400° C.

12. The process according to claim 11, further comprising the step of excluding oxygen from the first heating stage.

13. The process of claim 1 wherein step (3) comprises catalytic cracking.

* * * * *